United States Patent
Piijl et al.

(10) Patent No.: US 10,188,322 B2
(45) Date of Patent: Jan. 29, 2019

(54) METHOD AND APPARATUS FOR DETERMINING THE ORIENTATION OF AN ACCELEROMETER

(71) Applicant: KONINKLIJKE PHILIPS N.V., Eindhoven (NL)

(72) Inventors: Marten Jeroen Piijl, Eindhoven (NL); Johannes Henricus Maria Korst, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 118 days.

(21) Appl. No.: 15/108,608

(22) PCT Filed: May 7, 2015

(86) PCT No.: PCT/EP2015/060004
§ 371 (c)(1),
(2) Date: Jun. 28, 2016

(87) PCT Pub. No.: WO2015/169880
PCT Pub. Date: Nov. 12, 2015

(65) Prior Publication Data
US 2018/0192917 A1    Jul. 12, 2018

(30) Foreign Application Priority Data

May 9, 2014    (EP) .................................... 14167765

(51) Int. Cl.
*A61B 5/00*    (2006.01)
*A61B 5/11*    (2006.01)
(Continued)

(52) U.S. Cl.
CPC ............. *A61B 5/112* (2013.01); *A61B 5/1118* (2013.01); *A61B 5/1121* (2013.01);
(Continued)

(58) Field of Classification Search
CPC .......... A61B 5/11; A61B 5/112; A61B 5/1123
See application file for complete search history.

(56) References Cited

U.S. PATENT DOCUMENTS 8,880,377 B2 *  11/2014  Niemimaki ..........  G01C 22/006
                                                702/141
9,121,714 B2 *  9/2015  Janardhanan ........  G01C 21/165
(Continued)

FOREIGN PATENT DOCUMENTS

CN    101226061 A    7/2008
CN    103675338 A    3/2014

OTHER PUBLICATIONS

Buracchio et al: "The Trajectory of Gait Speed Preceding Mild Cognitive Impairement": Archives of Neurology Aug. 2010, vol. 67, Issue 8, pp. 980-986.
(Continued)

*Primary Examiner* — Max Hindenburg (57) ABSTRACT

There is provided a method of determining the orientation of an accelerometer that is being carried or worn by a user, the method comprising measuring acceleration using the accelerometer as the user moves; processing the measured acceleration to determine a step frequency of the movements by the user; and processing the measured acceleration to identify a lateral component of acceleration as a component of acceleration having a high response at a frequency corresponding to half the step frequency.

15 Claims, 4 Drawing Sheets

(51) Int. Cl.
  G01C 22/00 (2006.01)
  G06K 9/00 (2006.01)
  G01C 25/00 (2006.01)

(52) U.S. Cl.
  CPC .......... *A61B 5/6822* (2013.01); *A61B 5/7246* (2013.01); *G01C 22/006* (2013.01); *G01C 25/005* (2013.01); *G06K 9/00342* (2013.01); *G06K 9/00348* (2013.01); *A61B 5/1123* (2013.01); *A61B 2562/0219* (2013.01)

(56) References Cited

U.S. PATENT DOCUMENTS

| | | | |
|---|---|---|---|
| 9,186,096 B2 * | 11/2015 | Solinsky | A61B 5/112 |
| 9,700,241 B2 * | 7/2017 | Eastman | A61B 5/112 |
| 9,833,375 B2 * | 12/2017 | Miyake | A61H 3/00 |
| 2004/0230138 A1 | 11/2004 | Inoue et al. | |
| 2006/0284979 A1 | 12/2006 | Clarkson | |
| 2010/0161271 A1 | 6/2010 | Shah et al. | |
| 2012/0136573 A1 | 5/2012 | Janardhanan et al. | |
| 2012/0296221 A1 | 11/2012 | Morren | |
| 2013/0190008 A1 | 7/2013 | Vathsangam et al. | |
| 2013/0190658 A1 | 7/2013 | Flaction et al. | |

OTHER PUBLICATIONS

Shinkai et al: "Walking Speed As a Good Predictor for the Onset of Functional Dependence in a Japanese Rural Community Population"; Age and Ageing, 2000, vol. 29(5), pp. 441-446.

\* cited by examiner

METHOD AND APPARATUS FOR DETERMINING THE ORIENTATION OF AN ACCELEROMETER

CROSS-REFERENCE TO PRIOR APPLICATIONS

This application is the U.S. National Phase application under 35 U.S.C. § 371 of International Application No. PCT/EP2015/060004, filed on May 7, 2015, which claims the benefit of European Patent Application No. 14167765.8, filed on May 9, 2014. These applications are hereby incorporated by reference in their entirety herein.

TECHNICAL FIELD OF THE INVENTION

The invention relates to apparatus comprising an accelerometer that is being carried or worn by a user, and in particular relates to a technique for determining the orientation of the accelerometer, particularly a lateral component of acceleration in the reference frame of a user.

BACKGROUND TO THE INVENTION

A person's gait describes the characteristics of their walking behaviour. More formally, gait is defined as the way locomotion is achieved through use of the legs. While gait appears similar from person to person, there are in fact a number of differences between individuals, so much so that a person's gait can be considered unique, with gait features being used for security applications. Common examples of gait features include walking speed, cadence, step size and body sway, but gait can also include minor features such as the angle of the toes.

Walking is a complex operation, involving the musculoskeletal system, processing of sensory information, coordination and balance. If one or more of these systems becomes compromised, this will likely be reflected in changes to a person's gait. It is therefore not surprising that gait can be related to a person's health. Some studies have found strong correlations between walking speed and becoming functionally dependent in the future. Gait has also been linked to cognitive decline such as Alzheimer's disease.

Gait features can be measured with high accuracy with apparatus such as walking mats and motion capture cameras, but can also be approximated using more portable apparatus, such as those comprising accelerometers which can be placed at various points on the body. An accelerometer measures the acceleration occurring during the movement of the user (and also the force of gravity) along three orthogonal measurement axes, and the measurements can be processed to identify the vertical, forward and lateral components of acceleration experienced by the user. The forward component of acceleration can be used to estimate walking speed, while step length can be estimated through the use of an 'inverted pendulum' model, which also makes use of vertical displacement.

Ideally, the accelerometer is carried or worn by the user in such a way that the orientation of the accelerometer with respect to the user does not change during movement, and the orientation of the accelerometer with respect to the user is known so that the measurements along the measurement axes can be transformed (i.e. rotated) to the reference frame of the user (i.e. the vertical, forward and lateral directions). Even more ideally, the orientation of the accelerometer with respect to the user is such that the measurement axes of the accelerometer align with the vertical, forward and lateral directions of the user, avoiding the need for a transformation to be performed.

In practice though, the three accelerometer axes will rarely be precisely aligned with the vertical, lateral and forward directions. This is especially true where the accelerometer is not fixedly attached to the user's body, e.g. those carried in pockets or worn as a pendant.

It is possible to estimate the vertical component of the acceleration signal, making use of the constant acceleration caused by gravity, but it is difficult to tell the difference between the lateral and forward accelerations without knowing the orientation of the accelerometer. Rotations along the accelerometer's measurement axes cause no measureable acceleration, so knowing the orientation of the accelerometer is difficult without the aid of additional sensors, such as gyroscopes and/or magnetometers, which are both sensors with comparatively high power requirements.

US 2010/0161271 describes techniques for determining orientation of a three-axis accelerometer in which acceleration due to gravity is measured on each axis x, y, z of the accelerometer and the direction of gravity is used to associate or align the x-axis of the accelerometer with gravity, the acceleration not due to gravity is then used to identify the forward motion and to associate or align the forward direction with the y-axis. The remaining direction may be identified as the sideways direction, which may be associated or aligned with the z-axis. The forward motion can be identified as the accelerometer axis that has the greatest energy.

A disadvantage with the technique in US 2010/0161271 is that it is based on the assumption that the (non-vertical) component with the highest energy is the forward component. However, this assumption only holds for normal walking speeds (e.g. 5 km/h and above). At lower walking speeds, the energy of the forward and lateral components become increasingly similar, which makes it difficult, if not impossible, to distinguish the components using this technique.

Therefore there is a need for an alternative technique for determining the lateral component of acceleration from acceleration measurements.

SUMMARY OF THE INVENTION

According to a first aspect of the invention, there is provided a method of determining the orientation of an accelerometer that is being carried or worn by a user, the method comprising measuring acceleration using the accelerometer as the user moves; processing the measured acceleration to determine a step frequency of the movements by the user; and processing the measured acceleration to identify a lateral component of acceleration as a component of acceleration having a high response at a frequency corresponding to half the step frequency.

Preferably, the lateral component of acceleration is a lateral component of acceleration in the reference frame of the user.

The step frequency is the frequency with which the user takes steps while walking.

In some embodiments, the step of processing the measured acceleration to identify a lateral component of acceleration comprises transforming the acceleration measurements to the frequency domain and identifying the lateral component of acceleration as the component of acceleration having a high response at a frequency equal to or within a predetermined range of half the step frequency.

In those embodiments, the high response preferably comprises a response above a threshold value.

In alternative, preferred, embodiments, the step of processing the measured acceleration to identify a lateral component of acceleration comprises determining a set of rotation angles for the measured acceleration that minimises the autocorrelation of the measured acceleration in a particular direction at an autocorrelation lag that is at or around half the step frequency; wherein the lateral component of acceleration comprises the measured acceleration in the particular direction.

Preferably, the step of determining comprises (i) determining the autocorrelation of the measured acceleration; (ii) calculating the autocorrelation slope and determining the direction in which the steepest angle of descent in the autocorrelation occurs; (iii) update a set of rotation angles to effect a rotation of the measurement space to reduce the angle between the y-axis in the measurement space and the determined direction; (iv) determine the autocorrelation of the acceleration in the rotated measurement space; (v) if the autocorrelation of the acceleration in the rotated measurement space is less than the autocorrelation determined in step (i), rejecting the update to the set of rotation angles in step (iii) and repeating steps (iii) and (iv) with a smaller rotation of the measurement space; (vi) if the autocorrelation of the acceleration in the rotated measurement space is greater than the autocorrelation determined in step (i), determine the difference between the autocorrelation determined in step (iv) and the autocorrelation determined in step (i); and (vii) repeat steps (ii) to (vi) if the difference is greater than a threshold value, otherwise determining the acceleration in the direction in which the steepest angle of descent occurs in the rotated measurement space to be the lateral component of acceleration.

In some embodiments, the step of processing the measured acceleration to determine a step frequency of the movements by the user comprises computing the magnitude of the measured acceleration; and using a peak detection algorithm to find the step frequency in the frequency domain.

In alternative embodiments, the step of processing the measured acceleration to determine a step frequency of the movements by the user comprises computing the magnitude of the measured acceleration; calculating the autocorrelation of a signal representing the magnitude of the measured acceleration; identifying the maximum autocorrelation of the signal; and identifying a step time for the user as the lag corresponding to the maximum autocorrelation of the signal.

In some embodiments the method further comprises the steps of processing the measured acceleration to determine if the user is walking; and processing the measured acceleration to identify a lateral component of acceleration if the user is determined to be walking.

In some embodiments the step of processing the measured acceleration to determine if the user is walking comprises determining if the determined step frequency is within a predetermined range.

According to a second aspect of the invention, there is provided a computer program product having computer readable code embodied therein, the computer readable code being configured such that, on execution by a suitable computer or processing unit, the computer or processing unit is caused to perform any of the methods described above.

According to a third aspect of the invention, there is provided an apparatus for determining the orientation of an accelerometer that is carried or worn by a user, the apparatus comprising a processing unit that is configured to receive measurements of acceleration from the accelerometer, process the measured acceleration to determine a step frequency of movements by the user; and process the measured acceleration to identify a lateral component of acceleration as a component of acceleration having a high response at a frequency corresponding to half the step frequency.

Preferably, the lateral component of acceleration is a lateral component of acceleration in the reference frame of the user.

The step frequency is the frequency with which the user takes steps while walking.

In some embodiments, the processing unit is configured to process the measured acceleration to identify a lateral component of acceleration by transforming the acceleration measurements to the frequency domain and identifying the lateral component of acceleration as the component of acceleration having a high response at a frequency equal to or within a predetermined range of half the step frequency.

In those embodiments, the high response preferably comprises a response above a threshold value.

In alternative, preferred, embodiments, the processing unit is configured to process the measured acceleration to identify a lateral component of acceleration by determining a set of rotation angles for the measured acceleration that minimises the autocorrelation of the measured acceleration in a particular direction at an autocorrelation lag that is at or around half the step frequency; wherein the lateral component of acceleration comprises the measured acceleration in the particular direction.

Preferably, the processing unit is configured to process the measured acceleration to identify a lateral component of acceleration by (i) determining the autocorrelation of the measured acceleration; (ii) calculating the autocorrelation slope and determining the direction in which the steepest angle of descent in the autocorrelation occurs; (iii) update a set of rotation angles to effect a rotation of the measurement space to reduce the angle between the y-axis in the measurement space and the determined direction; (iv) determine the autocorrelation of the acceleration in the rotated measurement space; (v) if the autocorrelation of the acceleration in the rotated measurement space is less than the autocorrelation determined in step (i), rejecting the update to the set of rotation angles in step (iii) and repeating steps (iii) and (iv) with a smaller rotation of the measurement space; (vi) if the autocorrelation of the acceleration in the rotated measurement space is greater than the autocorrelation determined in step (i), determine the difference between the autocorrelation determined in step (iv) and the autocorrelation determined in step (i); and (vii) repeat steps (ii) to (vi) if the difference is greater than a threshold value, otherwise determining the acceleration in the direction in which the steepest angle of descent occurs in the rotated measurement space to be the lateral component of acceleration.

In some embodiments, the processing unit is configured to process the measured acceleration to determine a step frequency of the movements by the user by computing the magnitude of the measured acceleration; and using a peak detection algorithm to find the step frequency in the frequency domain.

In alternative embodiments, the processing unit is configured to process the measured acceleration to determine a step frequency of the movements by the user by computing the magnitude of the measured acceleration; calculating the autocorrelation of a signal representing the magnitude of the measured acceleration; identifying the maximum autocorrelation of the signal; and identifying a step time for the user as the lag corresponding to the maximum autocorrelation of the signal.

In some embodiments the processing unit is further configured to process the measured acceleration to determine if the user is walking; and process the measured acceleration to identify a lateral component of acceleration if the user is determined to be walking.

In some embodiments the processing unit is configured to process the measured acceleration to determine if the user is walking by determining if the determined step frequency is within a predetermined range.

In some embodiments, the processing unit is part of a device that further comprises the accelerometer, and the device is configured to be worn or carried by the user.

In alternative embodiments, the apparatus comprises a sensor unit that is separate to the processing unit, wherein the sensor unit comprises an accelerometer and is configured to be worn or carried by the user.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
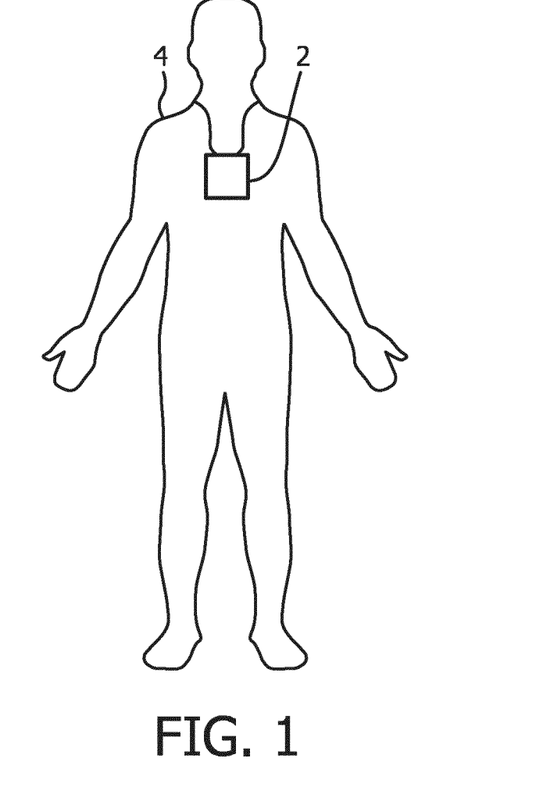
FIG. 1 is illustration of a device according to the invention being worn as a pendant.
Figure 2:
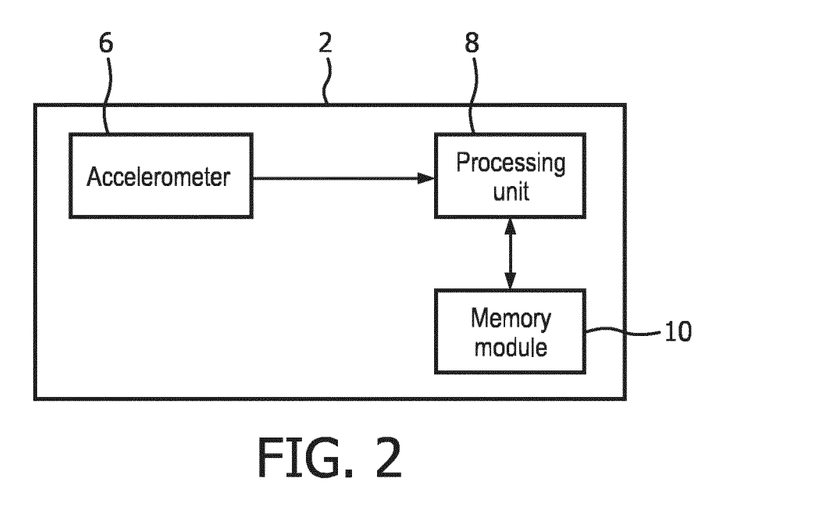
FIG. 2 is a block diagram of a device according to an embodiment of the invention.

FIG. 1 shows a device 2 in the form of a pendant that is worn around the neck of a user 4 and FIG. 2 is a block diagram of the device 2. The device 2 can be any type of device where it is necessary or useful to know the orientation of the device with respect to the horizontal plane. In some embodiments the device 2 is an activity monitor that monitors the physical activity of the user 4, for example for personal fitness purposes, or for supporting injury or fall prevention, for example during walking. The device 2 may be for monitoring steps or walking by the user 4 and identifying gait parameters, including where the parameters are used as a biometric for identifying an individual, or the device 2 may be for detecting other forms of traversing to walking, such as running, hopping, etc.). In other embodiments, the device 2 can be used for other purposes, for example it can be a step counter, a velocity monitor, a stability monitor, a fall detector or a smart phone.

The device 2 comprises at least one accelerometer 6 that measures the movements of the device 2 and that is in a fixed relationship with respect to the rest of the device 2 (i.e. the accelerometer 6 does not move in the device 2). The at least one accelerometer 6 measures the magnitude and direction of the acceleration acting on the device 2. The accelerometer 6 measures the accelerations in three dimensions and outputs a signal for three orthogonal axes (e.g. denoted x, y and z axes) indicating the magnitude of the acceleration acting along that axis over time. The accelerometer 6 measures the acceleration at a predetermined sampling frequency, for example 50 Hz, although other sampling frequencies can be used. It will be appreciated that instead of an accelerometer 6 that measures acceleration in three dimensions, the device 2 can comprise three accelerometers that measure the acceleration in one direction that are arranged orthogonally or roughly orthogonally to each other.

The device 2 further comprises a processing unit 8 that receives the acceleration measurements from the accelerometer 6 and processes the measurements to determine the orientation of the device 2. In some embodiments, the processing unit 8 determines the orientation of the device 2 in order to identify one or more of the vertical, forward and lateral components of acceleration in the acceleration measurements.

The device 2 also comprises a memory module 10 that can be used to store computer readable code or instructions for execution by the processing unit 8 in order to cause the processing unit 8 to process the acceleration measurements according to the invention. The memory module 10 can also be used to store the acceleration measurements before, during and after the processing by the processing unit 8 and any intermediate products of the processing.

Although in the preferred embodiment of the invention the device 2 is in the form of a pendant to be worn on a cord or thread around the neck of a user 4, it will be appreciated that the device 2 can be implemented in alternative forms that are to be worn on or carried by different parts of the body of the user 4, such as at the waist, on the chest, arm, wrist, leg or ankle.

In this illustrated embodiment of the invention, the device 2 comprises a single unit that is worn by the user 4 and that collects and processes the acceleration measurements. In alternative embodiments, the processing of the measurements can be performed in a unit that is remote from the accelerometer 6 (for example a unit that is worn on a different part of the body of the user 4, a base unit or computer that can be located in the user's home, or a remote server located in the premises of a healthcare service provider), in which case the device 2 will comprise a sensor unit to be worn by the user 4 that comprises suitable transmitter or transceiver circuitry for transmitting the measurements to the remote unit. In this embodiment, there is no need for the user-worn sensor unit to include a processing unit that is capable of processing the measurements to determine the orientation of the sensor unit.

It will be appreciated that in practical implementations, the device 2 may comprise other or further components to those shown in FIG. 2 and described above, such as a user interface that allows the user to activate and/or operate the device 2, and a power supply, such as a battery, for powering the device 2.

Although it is not currently feasible to establish the full orientation of an accelerometer (i.e. including the lateral and forward components) in all circumstances based on acceleration measurements alone, it has been found that it is possible to establish the full orientation of an accelerometer when the user is walking. In particular, the invention takes advantage of the gait (i.e. walking patterns) of the user since walking is, by nature, a highly cyclic pattern, and successive steps are highly similar to one another, and as such, the corresponding measurements of acceleration are also highly similar as well.

Figure 3:
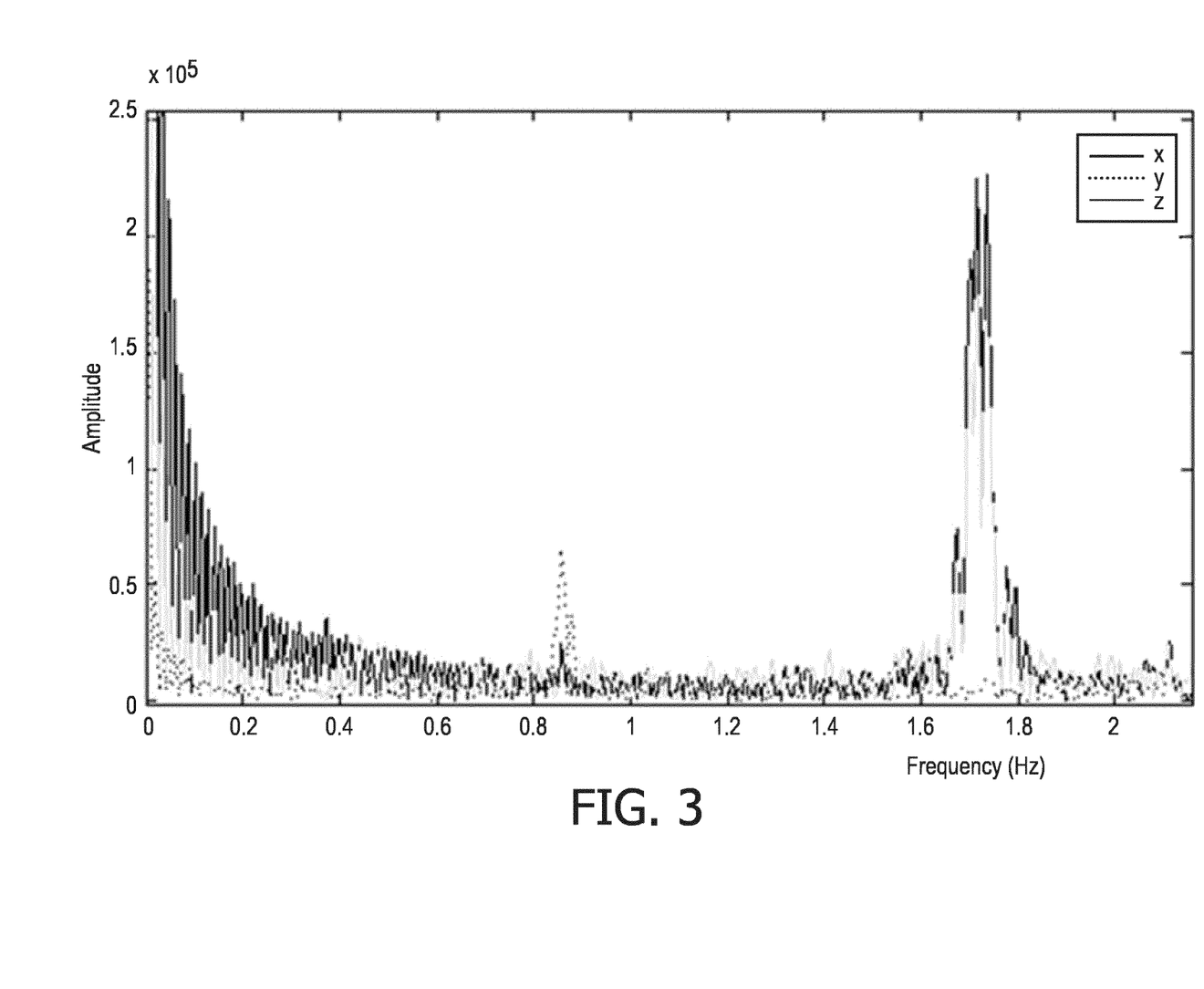
FIG. 3 is a graph illustrating the frequency amplitudes of acceleration measurements for three measurement axes of an accelerometer obtained while a wearer of the accelerometer is walking.

FIG. 3 is a graph showing the frequency amplitudes (i.e. amplitudes in the frequency domain) of acceleration measurements for three individual measurement axes (x-, y- and z-) obtained while the wearer of the accelerometer is walking. In this Figure, the x-axis is known to correspond to the vertical direction, the y-axis is known to correspond to the lateral direction and the z-axis is known to correspond to the forward direction. It can be seen from the analysis in the frequency domain that the x- and z-axes show a high frequency response (i.e. a peak or a high magnitude/amplitude in the frequency spectrum of the acceleration signal) which matches (i.e. occurs at) the step frequency (i.e. the frequency with which the user's feet strike the ground while walking, approximately 1.7 Hz in this case). In the general case where none of the measurement axes are aligned or closely aligned to the lateral direction, all three axes will show a high frequency response (i.e. a high response or a peak in the frequency domain) which matches (i.e. occurs at) the step frequency.

It can also be seen from FIG. 3 that the lateral (y-) component also shows a response (i.e. peak) at half the step frequency. This response is due to the fact that, regardless of whether a step is made with the left or right foot, the forward and vertical accelerations will be roughly similar. The lateral motion however corresponds to the user swaying alternately from left to right, which yields an inverted signal for each step. This swaying results in a periodic signal with twice the period of the step time, and therefore at half its frequency (the step frequency).

Thus the inventors have found that the lateral component of acceleration can be found regardless of orientation by maximizing the frequency response (response in the frequency domain) of a component of acceleration at half the step frequency.

Clearly this technique avoids the need to use another sensor such as a gyroscope or magnetometer to determine the horizontal components of acceleration, and the increases in power consumption that the use of those sensors cause. A further advantage over gyroscope-based methods is there is no measurement drift which is common in gyroscopes. If the accelerometer changes orientation while walking, this can be corrected relatively quickly using the invention.

Figure 4:
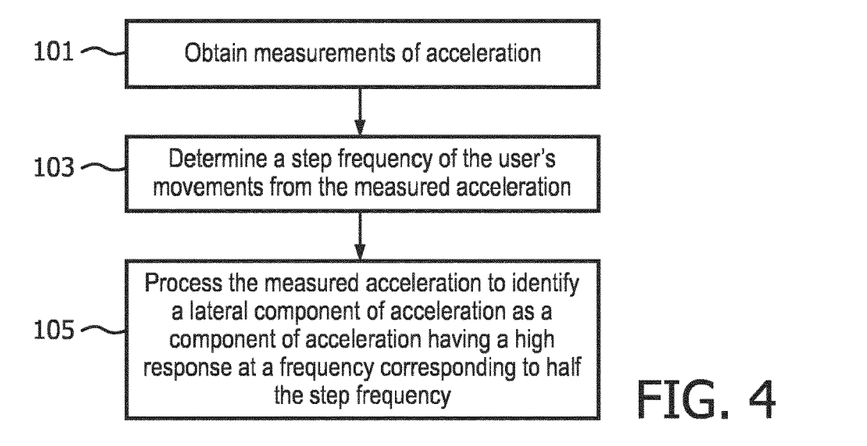
FIG. 4 is a flow chart illustrating a method according to an embodiment of the invention.

FIG. 4 is a flow chart illustrating a general embodiment of the invention. In a first step, step 101, measurements of acceleration are obtained using an accelerometer 6 that is being worn or carried by a user 4.

In step 103, a step frequency for the user's movements is determined from the acceleration measurements.

Those skilled in the art will be aware of various techniques for determining step frequency (or step time). In some implementations, the step time can be found by computing the magnitude of the accelerometer measurements, i.e.

$$\text{magnitude} = \sqrt{(a_x^2 + a_y^2 + a_z^2)}$$

and using a peak detection algorithm to find the step frequency in the frequency domain (which can of course be converted to step time). In this implementation, the magnitude signal is transformed to the frequency domain, and the highest value within the appropriate frequency band (e.g. 1-2.5 Hz) is selected.

In other implementations, autocorrelation can be used to find the step time. Auto correlation determines how well a signal correlates to itself shifted by a number of positions, known as 'lag'. A maximum autocorrelation of the time-domain magnitude signal can be identified within a certain lag interval (i.e. a range of acceptable lag), with the lag corresponding to the maximum autocorrelation providing the step time.

Those skilled in the art will be aware of other techniques or modifications to the above techniques (e.g. that the peak must be a certain amount above the noise level) that can be used to identify the step time or step frequency.

Once the step frequency/step time has been identified, the measured acceleration is processed to identify the lateral component of acceleration based on the finding that the lateral component of acceleration is a component of acceleration having a high response at a frequency corresponding to half the step frequency (step 105).

In some embodiments, the lateral component of acceleration can be found by transforming acceleration measurements to the frequency domain (for example using a fast Fourier transform) and identifying which of the axes has a high response in the frequency domain at a frequency equal to or around half the step frequency. The high response can be identified as a response (i.e. magnitude of the acceleration signal in the frequency domain) greater than a threshold value, or the axis with the highest response at a frequency equal to or around half the step frequency. In order to identify the lateral component of acceleration, the high response may be required to be found at exactly half the step frequency, or within a predetermined range of half of the step frequency. It will be appreciated that these embodiments are generally only reliable when one of the accelerometer axes is aligned or roughly aligned with the lateral direction, and precludes the finding of the lateral component of acceleration as a linear combination of the accelerometer axes. Thus these embodiments are not preferred in the general situation where the accelerometer 6 has an arbitrary orientation with respect to the user.

Figure 5:
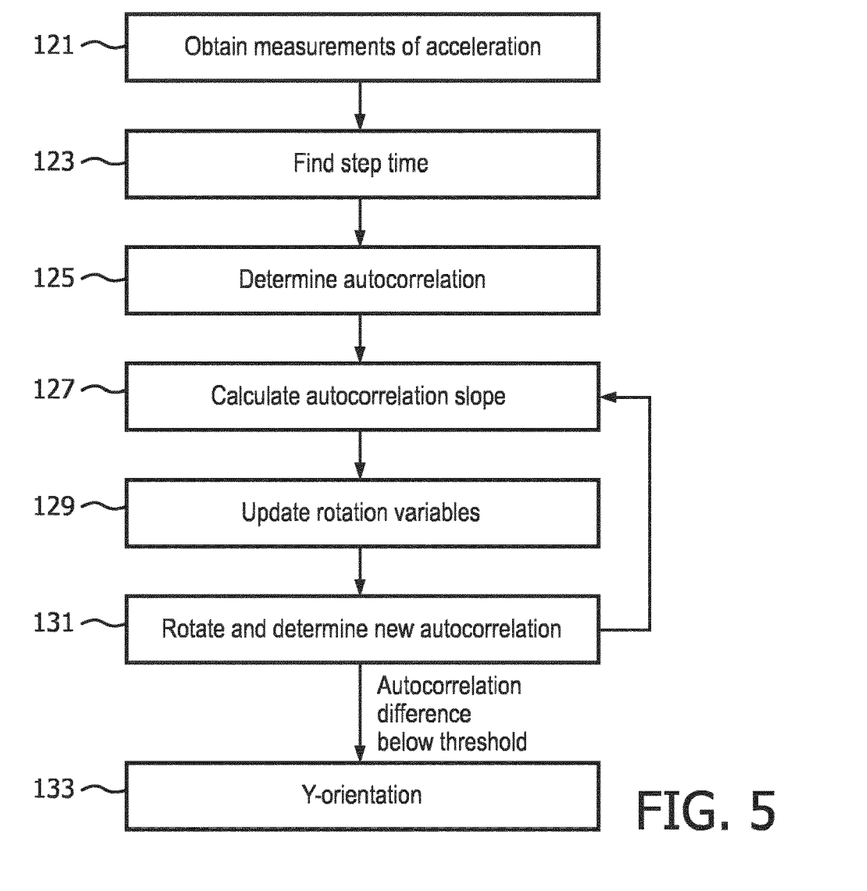
FIG. 5 is a flow chart illustrating a method according to a specific embodiment of the invention.

The flow chart in FIG. 5 illustrates a preferred embodiment of determining the lateral component of acceleration according to the invention. This algorithm is based on the principle that the lateral component of acceleration is the component of acceleration having a high response (peak) in the frequency domain at a frequency corresponding to half the step frequency, but uses autocorrelation rather than a transformation to the frequency domain (such as a fast Fourier transform), as using autocorrelation is computationally faster. With a lag equal to the step time, autocorrelation is expected to be positive for the forward and vertical components (as the acceleration signal repeats itself) and negative for the lateral component (as the acceleration signal is at half its period).

In step 121, acceleration measurements are obtained. Next, the step time or step frequency is determined (step 123). Step 123 can be performed as described above for step 103.

As noted above, the measurement axes of the accelerometer 6 are referred to as 'x', 'y' and 'z'. Ideally, the x-axis aligns with the vertical component (in the reference frame of the user), the y-axis aligns with the lateral component (in the user's frame of reference) and the z-axis aligns with the forward component (in the user's frame of reference), although alternative ideal orientations exist.

The aim of the method in FIG. 5 is to determine how the lateral component (in the user's frame of reference) can be formulated as a linear combination of the x, y, and z axes, by determining for which linear combination of the x, y, and z axes the response in the frequency domain at half the step frequency is maximal. To do so, the method of FIG. 5 provides that the accelerometer measurement axes are virtually rotated around the x- and z-axes until the y-axis aligns with the lateral component (rotating along the y-axis does not change the orientation of the y-axis itself). Since the x, y and z axes are orthogonal to each other, they can be viewed as a 3D Cartesian coordinate space; that is the general three-dimensional space where points are given by a vector of three values that indicate their distance from the origin along the respective axes. The methods used to rotate a Cartesian space can also be used to rotate (virtually) the accelerometer measurement axes (hence the term 'rotating the space' in the following description).

Rotation of a point in a 3D Cartesian space is a linear transformation, i.e. it can be achieved by multiplying a 3×3 rotation matrix with the 3D coordinate of the point. There are a number of ways of deriving such a matrix from a set of rotation parameters, for instance by deriving it from three rotation values along the x, y, and z axes respectively. By applying the rotation to each set of (x, y, z) accelerometer measurements, the accelerometer axes are effectively rotated to a new, virtual set of axes, which can for instance be called x', y', and z'. The aim is then to find a set of rotation angles such that y' is aligned with the lateral component.

Thus, to find the lateral component of acceleration, the autocorrelation of the signal along the y-axis is minimised by rotating the three-dimensional space along the x- and z-axes. This leads to the y-axis being aligned with the lateral component.

To find the lateral component, the autocorrelation of the acceleration measurements is determined for each of the measurement axes of the accelerometer 6 (step 125) and the slope of the autocorrelation is calculated (step 127). Minimizing the autocorrelation can be achieved using a hill-climbing algorithm which involves determining the steepest angle of descent given the current space orientation.

Once the steepest angle of descent is determined for the current space orientation, the rotation variables are updated in order to effect a rotation of the space such that the angle between the y-axis of the measurement space (in it's current orientation) and the determined direction is reduced (step 129).

Then, in step 131, the space is rotated using the updated rotation variables and the autocorrelation is recalculated. The process then returns to step 127 where the slope of the autocorrelation is determined.

Steps 127-131 are repeated until no more significant decreases in autocorrelation can be obtained. In some embodiments, this is determined by the difference between the recalculated autocorrelation and the previous autocorrelation value being less than a threshold value (i.e. after step 131 the difference between the recalculated autocorrelation and the previous autocorrelation value is determined, and if this difference is greater than the threshold value then the method returns to step 127, otherwise the method moves to step 133). In some embodiments, if the recalculated autocorrelation is less than the previous autocorrelation value, the update to the set of rotation angles/variables that led to the recalculated autocorrelation is rejected and a smaller rotation of the measurement space is effected instead.

Figure 6:
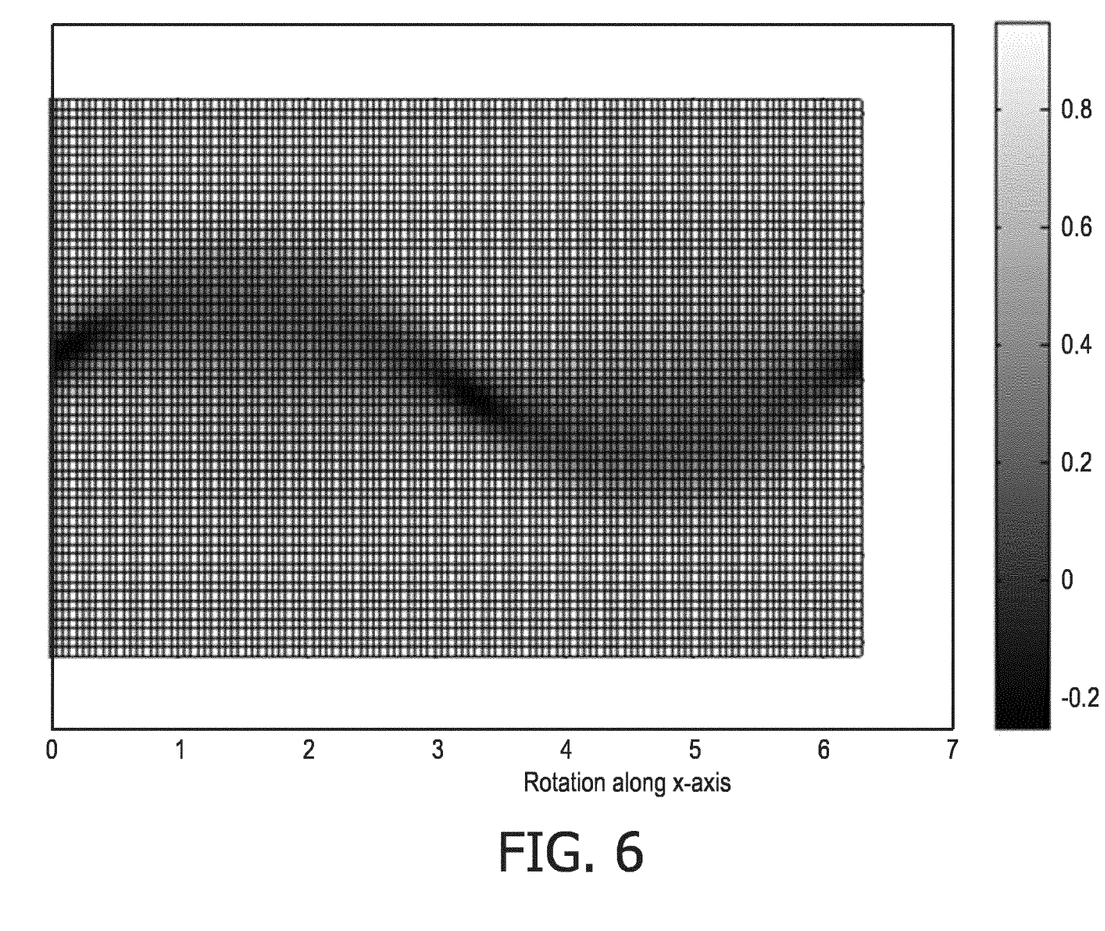
FIG. 6 is a heatmap showing the autocorrelation at the step time lag along the y-axis for all rotation possibilities along the x- and z-axes.

In step 133, it is determined that as no more significant decreases in autocorrelation can be obtained, the y-axis is aligned with the lateral component (as the autocorrelation-space is smooth, as shown in FIG. 6—which shows a heatmap of the autocorrelation at the step time lag along the y-axis for all rotation possibilities along the x- and z-axes). It will be noted from FIG. 6 that the lack of local minima or maxima allows a hill-descent-type algorithm to reliably find the optimal rotation that minimises the autocorrelation (rotation angles are given in radians).

Hill-climbing algorithm in steps 127-131: Hill-climbing is one of a possible number of ways to arrive at a set of rotation angles that maximises some criteria, in this case a large negative autocorrelation on the y-axis at the appropriate autocorrelation lag. The algorithm starts with an initial set of rotation angles, finds in which 'direction' the criteria improves the fastest (i.e. the steepest slope)—step 127, updates the rotation angles in this direction (step 129), and repeats until the criteria cannot be increased further.

As rotation along the y-axis will not affect its orientation, only rotation along the x and z axes needs to be considered. These two rotation values can be considered as a two-dimensional point in space, which can move in a certain direction by changing the values. To estimate the slope (step 127), for example, four points around the rotation values can be chosen, two on either side of the x-rotation, and two on either side of the z-rotation. The new points should be fairly close to the original point.

The criteria scores can then be calculated for the new points, the point with the highest criteria score can be found, and a certain distance can be moved in that direction. In practice, step 129 comprises adding or subtracting some value from one of the rotation angles and updating the rotation matrix, and step 131 comprises computing a new rotation and determining autocorrelation values. This can either be a fixed value, or some formula can be used to derive a distance value. The direction moved in can be a composite of directions which improved the criteria. Also, more than four points can be used if desired.

If the new set of rotation angles is an improvement, this set is kept and the process to select four new points starts again. If it is not an improvement, the new points are rejected, a smaller distance movement in the same direction is tried instead. The algorithm is ended when no substantial improvements are made, either because no directions can be found that yield improvement, or because the distance travelled has become so small that no real progress is made.

The initial set of rotation angles can be important, but if the search space is such that the highest criterion is always found from any initial position, this is not a concern. It can be seen from FIG. 6 that this is the case here. Practically this means that the algorithm always aligns with the lateral component, regardless of the original orientation of the y-axis.

Once the lateral component of acceleration is obtained in step 105 or 133, the vertical and forward components can then be aligned through gravity-estimation techniques, which are known in the art. In particular, gravity-estimation techniques can be used to identify the vertical component of acceleration, which leaves the remaining component as the forward component. Alternatively, it is possible to determine the vertical component using such techniques before attempting to identify the lateral component, and then find the lateral component through the techniques described above. In some cases finding the vertical component first is more advantageous, as there are less degrees of freedom when finding the lateral component, particularly where the rotation matrix is 'brute forced' (i.e. the best autocorrelation is computed for a fixed set of rotation angles).

It will be appreciated that the method according to the invention is effective when the user is walking or performing a similar type of movement (e.g. jogging, running, etc.). Therefore, in any of the above embodiments, a check of the acceleration measurements can be performed to determine if the user's movements correspond to walking and thus whether the determined orientation of the accelerometer 6 can be considered reliable. This check can be performed at any point in the above methods, for example prior to step 103 in the embodiment of FIG. 4 and prior to step 123 in the embodiment of FIG. 5. This check of the acceleration measurements can comprise, for example, performing pattern matching of the acceleration measurements to known patterns for walking, or checking for a step frequency in an appropriate band (e.g. 1-2.5 Hz), although those skilled in the art will be aware of other techniques that can be used to identify if the user is walking from the accelerometer measurements. It will be appreciated that the second of these examples would be performed after step 103 in FIG. 4 and step 123 in FIG. 5. If the test suggests that the user is not walking (or jogging, running, etc.), the processing of the acceleration measurements to determine the lateral orientation can be stopped or the determined orientation discarded as unreliable.

There is therefore provided a technique that can reliably identify the lateral component of acceleration in acceleration measurements by an accelerometer that is attached to or being carried by a user that is walking.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining the orientation of an accelerometer that is being carried or worn by a user, the method comprising:
   measuring acceleration using the accelerometer as the user moves;
   processing the measured acceleration to determine a step frequency of the movements by the user; and
   processing the measured acceleration to identify a lateral component of acceleration as a component of acceleration having a high response at a frequency corresponding to half the step frequency.

2. The method as claimed in claim 1, wherein the step of processing the measured acceleration to identify a lateral component of acceleration comprises:
   determining a set of rotation angles for the measured acceleration that minimizes the autocorrelation of the measured acceleration in a particular direction at an autocorrelation lag that is at or around half the step frequency; wherein the lateral component of acceleration comprises the measured acceleration in the particular direction.

3. The method as claimed in claim 2, wherein the step of determining comprises:
   (i) determining the autocorrelation of the measured acceleration;
   (ii) calculating the autocorrelation slope and determining the direction in which the steepest angle of descent in the autocorrelation occurs;
   (iii) update a set of rotation angles to effect a rotation of the measurement space to reduce the angle between the y-axis in the measurement space and the determined direction;
   (iv) determine the autocorrelation of the acceleration in the rotated measurement space;
   (v) if the autocorrelation of the acceleration in the rotated measurement space is less than the autocorrelation determined in step (i), rejecting the update to the set of rotation angles in step (iii) and repeating steps (iii) and (iv) with a smaller rotation of the measurement space;
   (vi) if the autocorrelation of the acceleration in the rotated measurement space is greater than the autocorrelation determined in step (i), determine the difference between the autocorrelation determined in step (iv) and the autocorrelation determined in step (i); and
   (vii) repeat steps (ii) to (vi) if the difference is greater than a threshold value, otherwise determining the acceleration in the direction in which the steepest angle of descent occurs in the rotated measurement space to be the lateral component of acceleration.

4. The method as claimed in claim 1, wherein the step of processing the measured acceleration to identify a lateral component of acceleration comprises transforming the acceleration measurements to the frequency domain and identifying the lateral component of acceleration as the component of acceleration having a high response at a frequency equal to or within a predetermined range of half the step frequency.

5. The method as claimed in claim 1, wherein the step of processing the measured acceleration to determine a step frequency of the movements by the user comprises:
   computing the magnitude of the measured acceleration; and
   using a peak detection algorithm to find the step frequency in the frequency domain.

6. The method as claimed in claim 1, wherein the step of processing the measured acceleration to determine a step frequency of the movements by the user comprises:
   computing the magnitude of the measured acceleration;
   calculating the autocorrelation of a signal representing the magnitude of the measured acceleration;
   identifying the maximum autocorrelation of the signal; and
   identifying a step time for the user as the lag corresponding to the maximum autocorrelation of the signal.

7. The method as claimed in claim 1, further comprising the steps of:
   processing the measured acceleration to determine if the user is walking; and
   processing the measured acceleration to identify a lateral component of acceleration if the user is determined to be walking.

8. The method as claimed in claim 1, wherein the step of processing the measured acceleration to determine if the user is walking comprises determining if the determined step frequency is within a predetermined range.

9. A non-transitory computer readable medium encoded with computer readable instructions which when executed by a processor cause the processor to: receive an acceleration measurement measured using an accelerometer as a user moves, process the measured acceleration to determine a step frequency of the movements by the user, and process the measured acceleration to identify a lateral component of acceleration as a component of acceleration having a high response at a frequency corresponding to half the step frequency.

10. An apparatus, comprising:
an accelerometer carried or worn by a user; and
a processing unit that is configured to:
  receive measurements of acceleration from the accelerometer;
  process the measured acceleration to determine a step frequency of movements by the user; and
  process the measured acceleration to identify a lateral component of acceleration as a component of acceleration having a high response at a frequency corresponding to half the step frequency.

11. The apparatus as claimed in claim 10, wherein the processing unit is configured to process the measured acceleration to identify a lateral component of acceleration by:
  determining a set of rotation angles for the measured acceleration that minimizes the autocorrelation of the measured acceleration in a particular direction at an autocorrelation lag that is at or around half the step frequency; wherein the lateral component of acceleration comprises the measured acceleration in the particular direction.

12. The apparatus as claimed in claim 10, wherein the processing unit is configured to process the measured acceleration to identify a lateral component of acceleration by
  (i) determining the autocorrelation of the measured acceleration;
  (ii) calculating the autocorrelation slope and determining the direction in which the steepest angle of descent in the autocorrelation occurs;
  (iii) update a set of rotation angles to effect a rotation of the measurement space to reduce the angle between the y-axis in the measurement space and the determined direction;
  (iv) determine the autocorrelation of the acceleration in the rotated measurement space;
  (v) if the autocorrelation of the acceleration in the rotated measurement space is less than the autocorrelation determined in step (i), rejecting the update to the set of rotation angles in step (iii) and repeating steps (iii) and (iv) with a smaller rotation of the measurement space;
  (vi) if the autocorrelation of the acceleration in the rotated measurement space is greater than the autocorrelation determined in step (i), determine the difference between the autocorrelation determined in step (iv) and the autocorrelation determined in step (i); and
  (vii) repeat steps (ii) to (vi) if the difference is greater than a threshold value, otherwise determining the acceleration in the direction in which the steepest angle of descent occurs in the rotated measurement space to be the lateral component of acceleration.

13. The apparatus as claimed in claim 10, wherein the processing unit is configured to process the measured acceleration to determine a step frequency of the movements by the user by computing the magnitude of the measured acceleration; and using a peak detection algorithm to find the step frequency in the frequency domain.

14. The apparatus as claimed in claim 10, wherein the processing unit is configured to process the measured acceleration to determine a step frequency of the movements by the user by computing the magnitude of the measured acceleration; calculating the autocorrelation of a signal representing the magnitude of the measured acceleration; identifying the maximum autocorrelation of the signal; and identifying a step time for the user as the lag corresponding to the maximum autocorrelation of the signal.

15. The apparatus as claimed in claim 10, wherein the processing unit is further configured to process the measured acceleration to determine if the user is walking; and process the measured acceleration to identify a lateral component of acceleration if the user is determined to be walking.

* * * * *